(12) United States Patent
Kokubo et al.

(10) Patent No.: US 8,784,864 B2
(45) Date of Patent: Jul. 22, 2014

(54) BONE REPAIR MATERIAL AND METHOD FOR PRODUCING THE SAME

(75) Inventors: Tadashi Kokubo, Kasugai (JP); Tomiharu Matsushita, Kasugai (JP); Deepak K. Pattanayak, Kasugai (JP)

(73) Assignees: Chubu University Educational Foundation, Kasugai-shi (JP); Osaka Yakin Kogyo Co., Ltd, Osaka (JP); Avanced Medix Inc., Kyoto (JP)

(*) Notice: Subject to any disclaimer, the term of this patent is extended or adjusted under 35 U.S.C. 154(b) by 154 days.

(21) Appl. No.: 13/147,082

(22) PCT Filed: Jan. 29, 2010

(86) PCT No.: PCT/JP2010/051196
§ 371 (c)(1),
(2), (4) Date: Jul. 29, 2011

(87) PCT Pub. No.: WO2010/087427
PCT Pub. Date: Aug. 5, 2010

(65) Prior Publication Data
US 2011/0287070 A1    Nov. 24, 2011

(30) Foreign Application Priority Data
Jan. 30, 2009   (JP) ................. 2009-019081

(51) Int. Cl.
*A61K 33/24* (2006.01)
*A61K 9/00* (2006.01)

(52) U.S. Cl.
USPC .............. 424/423; 424/400; 424/617; 606/76

(58) Field of Classification Search
USPC ............................ 424/423, 400, 617; 606/76
See application file for complete search history.

(56) References Cited

U.S. PATENT DOCUMENTS 5,609,633 A * 3/1997 Kokubo ................. 424/423
5,667,385 A * 9/1997 Hansson ................. 433/201.1
(Continued)

FOREIGN PATENT DOCUMENTS

EP   1 584 337 A1   10/2005
EP   1 825 828 A1    8/2007
(Continued)

OTHER PUBLICATIONS

Takemoto et al. Osteoinductive porous titanium implants: Effect of sodium removal by dilute HCl treatment. Dec. 29, 2005. Biomaterials. pp. 2682-2690.*

(Continued)

*Primary Examiner* — Lezah Roberts
*Assistant Examiner* — Tracy Liu
(74) *Attorney, Agent, or Firm* — Westerman, Hattori, Daniels & Adrian, LLP (57) ABSTRACT

Bone repair materials are disclosed, from which ions are hardly eluted in living body and which are superior in apatite-forming ability and resistance to apatite peeling and have a scratch resistance high enough for practical use. The material comprises a substrate made of titanium or titanium alloys, and a surface layer, made substantially of titanium oxide, along the surface of the substrate. The substrate has on the surface thereof irregularities of from 1 nm to 10 μm in average in both width and depth. The layer has a zeta potential of +4.5 mV or more under an aqueous solution environment of pH 6 to 8, and a critical scratch resistance of 35 mN or more when vibration 100 μm in amplitude is added to a stylus with a spring constant of 200 g/mm on the surface layer and the stylus is moved at a rate of 10 mm/sec under a load increasing at a rate of 100 mN/min.

8 Claims, 4 Drawing Sheets

(56) References Cited

U.S. PATENT DOCUMENTS

| | | |
|---|---|---|
| 6,652,765 B1 | 11/2003 | Beaty |
| 2009/0130632 A1 | 5/2009 | Tsuru et al. |

FOREIGN PATENT DOCUMENTS

| | | |
|---|---|---|
| JP | 2002-102330 A | 4/2002 |
| JP | 2006-238937 A | 9/2006 |
| JP | 2006-255319 A | 9/2006 |
| JP | 2007-159685 A | 6/2007 |
| KR | 20030038631 A | 5/2003 |
| WO | 95/13100 A1 | 5/1995 |

OTHER PUBLICATIONS

Kim et al. Surface potential change in bioactive titanium metal during the process of apatite formation in simulated body fluid. Jul. 15, 2003. Wiley Periodicals Inc. pp. 1305-1308.*

International Search Report for PCT/JP2010/051196, mailing date of Mar. 16, 2010.

Himeno T. et al., "Zeta-Potential Variation of Bioactive Titanium Metal during Apatite Formation on its Surface in Simulated Body Fluid", Key Engineering Materials, vols. 218-220, (2002), pp. 641-644.

Lee M. et al., "Evaluation of in vitro and in vivo tests for Surface-Modified titanium by H2SO4 and H2O2 Treatment", Metals and Materials International, vol. 13, No. 2, (2007), pp. 109-115.

Lu X. et al., "Spectroscopic analysis of titanium surface functional groups under various surface modification and their behaviors in vitro and in vivo", Journal of biomedical Materials Research Part A, (2007), pp. 523-534.

Kokubo H. et al., "Bioceramics and their clinical applications", Woodhead Pub., (2008), pp. 485-500.

Sugino A. et al., "Effect of spatial design and thermal oxidation on apatite formation on Ti-15Zr-4Ta-4Nb alloy", Acta Biomaterialia, (2009), pp. 298-304.

Wang X. et al., "Bioactive titania gel layers formed by chemical treatment of Ti substrate with a H2O2/HCl solution", Biomaterials, (2002), vol. 23, pp. 1353-1357.

Yang B. et al., "Preparation of bioactive titanium metal via anodic oxidation treatment", Biomaterials (2004), vol. 25, pp. 1003-1010.

Kizuki T. et al., "Improvement of Apatite-Forming Ability of Titanium Metal Enriched with Calcium Ion on Its Surface", Key Engineering, (2009), vol. 396-398, pp. 341-344.

Lu X. et al., "Biomimetic calcium phosphate coatings on nitric-acid-treated titanium surfaces", Materials Science and Engineering, (2007) vol. C27, pp. 700-708.

Extended European Search Report dated Feb. 26, 2014, issued in corresponding European application No. 10735889.7 (6 pages).

* cited by examiner

BONE REPAIR MATERIAL AND METHOD FOR PRODUCING THE SAME

TECHNICAL FIELD

The present invention relates to bioactive bone repair materials and methods for producing the same. These bioactive bone repair materials can be used suitably for bone repair at a portion to which a large load is applied, such as the femur, the hip joint, the vertebra, and the tooth root.

BACKGROUND ART

Titanium or alloys thereof on the surface of which an apatite layer. As formed are expected as a bone repair material to be used at a portion to which a large load is applied because they have a high fracture toughness and can bond to living bone via apatite in living body. Since an apatite layer beforehand formed out of living body is easily peeled off, there have been proposed various methods for producing a bone repair material of titanium or alloys thereof on the surface of which a titanate layer having an apatite-forming ability is formed in order to form apatite in the body and, at the same time, bond it to living bone (Patent Document 1, Non-Patent Document 1). Moreover, various methods for producing a bone repair material on which a layer of titanium oxide is formed have also been proposed (Patent Document 2, Non-Patent Documents 2-8).

PRIOR ART DOCUMENTS

Patent Documents

Patent Document 1: WO95/13100
Patent Document 2: JP3877505

Non-Patent Documents

Non-Patent Document 1: Kizuki, et al., Key Engineering, vol. 396-398, p 341-344 (2009)
Non-Patent Document 2: Kokubo, et al., Bioceramics and their clinical applications, Woodhead Pub., p 485-500 (2008)
Non-Patent Document 3: Wang, et al., Biomaterials, vol. 23, p 1353-1357 (2002)
Non-Patent Document 4: Yang, et al., Biomaterials, vol. 25, p 1003-1010 (2004)
Non-Patent Document 5: Lu, et al., Materials Science and Engineering, vol. C27, p 700-708 (2007)
Non-Patent Document 6: Lee, et al., Metals and Materials International, vol. 13, p 109-115 (2007)
Non-Patent Document 7: Lu, et al., J. Biomed. Mater. Res. vol. 84A, p 523-534 (2008)
Non-Patent Document 8: Sugino, et al., Acta Biomateriala, vol. 5, p 298-304 (2009)

DISCLOSURE OF THE INVENTION

Problems to be Solved by the Invention

However, a titanate layer as disclosed in Patent Document 1 or Non-Patent Document 1 allows sodium ions and calcium ions to be eluted from the surface thereof in living body, so that it disturbs a surrounding body fluid environment. On the other hand, among titanium oxide layers formed by the aforementioned various methods, layers formed on surfaces by finally treating with water or an acidic aqueous solution, as disclosed in Patent Document 2 or Non-Patent Documents 2 and 5-7, are poor in apatite-forming ability. Moreover, a surface layer formed by a hydrogen peroxide treatment as disclosed in Non-Patent Document 3 is low in scratch resistance. A surface layer formed by anodic oxidation as disclosed in Non-Patent Document 4 includes deep holes unevenly and is difficult to be sterilized because bacteria go into the holes. A layer formed on the surface of irregularities formed of scars as disclosed in Non-Patent Document 8 has a portion where apatite is not formed and, therefore, the layer is poor in uniformity of apatite-forming ability.

Therefore, an object of the present invention is to provide a bone repair material from which ions are hardly eluted in living body and which is superior in apatite-forming ability and resistance to apatite peeling and has a scratch resistance high enough for practical use.

Means for Solving the Problems

In order to solve this problem, the bone repair material of the present invention includes a substrate and a surface layer. The substrate has on the surface thereof irregularities of from 1 nm to 10 μm in average in both width and depth and is made of titanium or titanium alloys. The surface layer is formed along the surface of the substrate, is made substantially of titanium oxide, and has a zeta potential of +4.5 mV or more, preferably +5.0 mV or more, under an aqueous solution environment of pH 6 to 8.

According to the bone repair material of the present invention, since the surface layer is made of titanium oxide, ions are hardly eluted in living body. Moreover, since the surface layer is positively charged under an aqueous solution environment as described above, the surface layer is charged similarly even under an environment of a body fluid which is a kind of the aforementioned aqueous solution, and the surface layer causes phosphate ions and calcium ions to be adsorbed in this order. As a result, an apatite layer is formed on the whole surface of the surface layer within one day, or within three days at most. Moreover, the irregularities of from 1 nm to 10 μm in average will fulfill a function of strongly bonding, to a substrate, an apatite layer to be formed on the surface in living body and living bone bonded via the apatite layer. The phase of the titanium oxide may be of either rutile or anatase and also may be of other forms.

An appropriate method for producing the bone repair material of the present invention is characterized by preparing a substrate made of titanium or titanium alloys, forming irregularities of from 1 nm to 10 μm in average in both width and depth on the surface of the substrate, immersing the substrate in an acidic aqueous solution having a pH of 3 or less, washing the substrate with water, and heating the substrate.

The substrates to be prepared may be made of pure titanium and also may be made of titanium alloys, such as Ti-6Al-4V and Ti-15Zr-4Nb-4Ta.

Means for forming the aforementioned irregularities on the surface may be an alkali treatment or sandblasting. In the case of the alkali treatment, the surface layer of the substrate is modified into a phase of titanate simultaneously with the formation of irregularities, and the phase is further modified into a phase of titanic acid by subsequently being washed with water. In the case of sandblasting, the surface layer is modified into a titanium oxide phase by subsequently being subjected to an acid treatment or oxidation. One preferable means for the formation of irregularities is an alkali treatment. This is because uniform irregularities of 1 to 100 nm in average in width are thereby formed.

Figure 1:
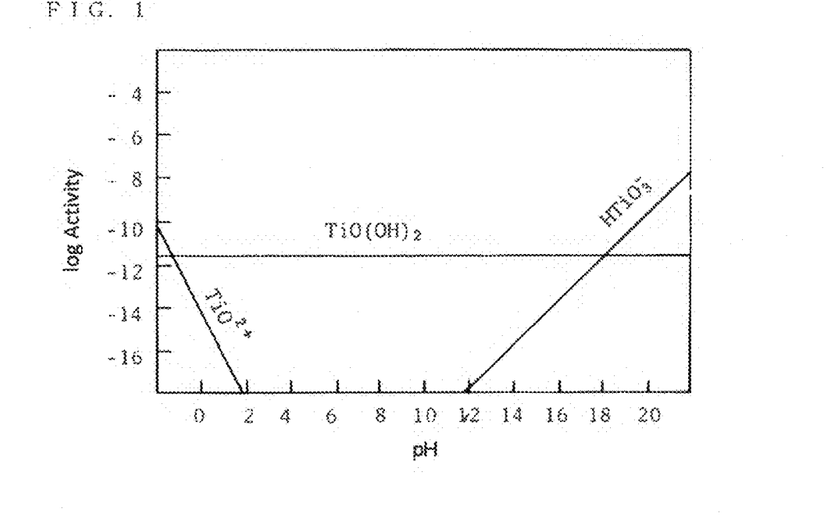
FIG. 1 is a graph showing the relation between the activities of titanium oxide and hydrates thereof and pH in an aqueous solution of 25° C.

Anyway, it is reported that titanium oxide is positively charged in an aqueous solution having a pH of 3 or less as shown in FIG. 1 (Takagi Hiroshi, et al., Yogyo Kyokaishi, vol. 88, p. 34-42 (1981)). Experiments done by the present inventors have shown that a titanium substrate that was immersed in an acidic aqueous solution having a pH of 3 or less, then washed with water to such a degree that anions derived from an acid were only slightly detected, and heated unexpectedly maintains a property to be positively charged even under an aqueous solution environment of pH 6 to 8. Then, the titanium substrate is converted by the heating into a layer superior in scratch resistance.

Examples of the aforementioned acidic aqueous solution include aqueous solutions of hydrochloric acid, sulfuric acid, nitric acid, fluoric acid, or mixed acid thereof. It is preferred that the temperature of the acidic aqueous solution be 0 to 100° C. and the immersion time be 0.5 to 100 hours.

That a surface layer is positively charged under an aqueous solution environment also means that acid groups which constitute an acid, such as sulfuric acid, nitric acid, hydrochloric acid, and fluoric acid, remain on the surface of titanium oxide.

The formation of the aforementioned irregularities may be conducted also by performing a treatment with an acidic aqueous solution that is the same as or different from the aforementioned acidic aqueous solution. If the same acidic aqueous solution is used, the formation of irregularities and the surface modification can be advanced simultaneously. Depending on the pH of the acidic aqueous solution and the time of treatment, relatively large and uniform irregularities having a width of from 1 μm to 10 μm in average can be formed by this method. The pH of an acidic aqueous solution that is preferred for the formation of irregularities is 1 or less.

In any production methods, controlling of a washing step is important. This is because in order to prevent harmful ions from being eluted into a body, it is necessary to do washing with water to such an extent that anions derived from an acid are possibly undetectable, but the zeta potential will be reduced to less than +4.5 mV if washing with water is done thoroughly to an excessive extent and thereby anions are made undetectable. A preferred washing time is from 10 seconds to 1 minute. However, when washing with hot water or running water, the washing time may be shorter than 10 seconds, whereas when washing with cold water, it may exceed 1 minute. The heating temperature after the washing with water is usually 450 to 750° C., preferably 500 to 700° C. If the temperature is lower than 450° C., the phase of the surface layer does not sufficiently change into titanium oxide, so that the surface thereof is not charged positively under a body fluid environment and also is low in scratch resistance. If the temperature exceeds 750° C., the surface layer of titanium oxide becomes thick due to penetration of a large amount of oxygen, so that the surface layer will become prone to be peeled off due to the difference in thermal expansion and, as a result, scratch resistance will deteriorate. The heat time is preferably 0.5 to 48 hours.

Effect of the Invention

As described above, the bone repair material of the present invention never injures living body because ions are hardly eluted therefrom in the living body. In addition, since the material has scratch resistance high enough for practical use, the surface layer is not peeled off when being implanted into living body. Moreover, since the material is superior in apatite-forming ability, it can bond to living bone rapidly to repair a bone defect. Furthermore, since the irregularities on the surface of the material are not very large and are uniform, the material does not vary in quality and is superior in reliability.

MODE FOR CARRYING OUT THE INVENTION

For an alkali treatment for forming irregularities, there can be used an aqueous solution of any of sodium hydroxide, potassium hydroxide and calcium hydroxide or a mixed solution thereof. The concentration, temperature, and time thereof are not limited. Generally, irregularities to be formed become deeper as the concentration becomes higher, the temperature becomes higher, and the time becomes longer. It is preferred to use, for a sandblast treatment, blast particles that do not impede a subsequent chemical treatment (an acid treatment or oxidation), such as calcium phosphate particles. Acid-resistant particles such as alumina particles are not preferable because they will remain on a surface to impede a subsequent acid treatment. For an acid treatment for forming irregularities, any of hydrochloric acid, sulfuric acid, nitric acid, and hydrofluoric acid, or a mixed acid thereof can be used. The concentration, temperature, and time thereof are not limited.

EXAMPLES

Production Conditions

Example 1

Figure 2:
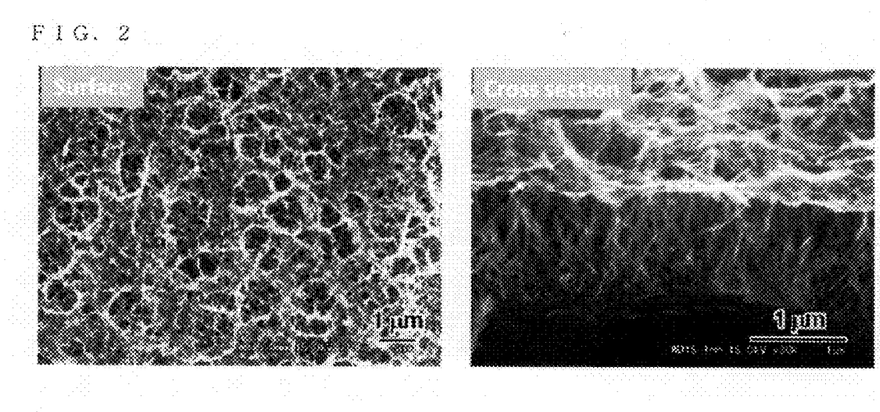
FIG. 2 is a scanning electron microphotograph of a titanium metal plate on which irregularities are formed on surfaces by an alkali treatment.

A pure titanium metal plate having a size of 10 mm×10 mm×1 mm was prepared, and polished with #400 diamond polishing paper in order to make the initial condition uniform. This plate was ultrasonically washed with acetone, 2-propanol, and ultrapure water each for 30 minutes sequentially, and then immersed in 5 ml of a 5 M aqueous sodium hydroxide solution at 60° C. for 24 hours (hereinafter, referred to as an "alkali treatment"), so that irregularities having an average depth of 1 μm and an average diameter of 17 nm were formed on the surface of the plate as depicted in FIG. 2. Subsequently, the plate was immersed in 10 ml of a 50 mM aqueous hydrochloric acid (HCl) solution having a pH of 1.47, at 40° C. for 24 hours and was washed with ultrapure water of 25° C. for 30 seconds. Then, the plate was put into a SiC electric furnace, heated in air up to 600° C. at a rate of 5° C./min, held at 600° C. for one hour, and then allowed to cool in the furnace, so that a bone repair material specimen was obtained.

Example 2

A specimen was produced under the same conditions as those used in Example 1 except for adjusting the holding temperature of the electric furnace to 700° C.

Example 3

A specimen was produced under the same conditions as those used in Example 1 except for using a 50 mM aqueous nitric acid ($HNO_3$) solution having a pH of 1.46 instead of the aqueous HCl solution as an acidic aqueous solution.

Example 4

A specimen was produced under the same conditions as those used in Example 1 except for using a 10 mM aqueous sulfuric acid ($H_2SO_4$) solution having a pH of 1.98 instead of the aqueous HCl solution as an acidic aqueous solution.

Example 5

Figure 3:
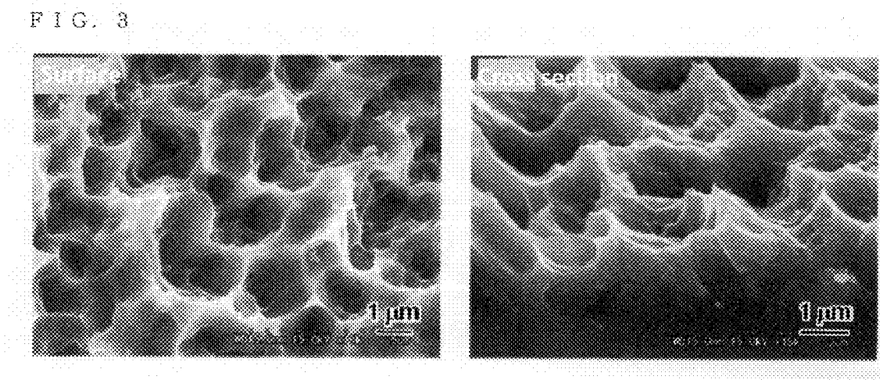
FIG. 3 is a scanning electron microphotograph of a titanium metal plate on which irregularities are formed on surfaces by an acid treatment.

A pure titanium metal plate in the same size as that of Example 1 was polished and washed in the same manner as in Example 1. Then, the plate was immersed in 20 ml of a mixed liquid made up of a 66.3 wt % aqueous sulfuric acid $H_2SO_4$ solution and a 10.6 wt % aqueous hydrochloric acid HCl solution at 70° C. for one hour, so that irregularities having an average depth of 1 μm and an average hole diameter of 1 μm were formed on the surface thereof as depicted in FIG. 3. The pH of the mixed liquid was close to 0. A specimen was produced by washing this titanium metal plate with ultrapure water in the same manner as in Example 1 and heating it at 600° C.

Comparative Example 1

A specimen was produced under the same conditions as those used in Example 1 except for using a 0.5 mM aqueous hydrochloric acid HCl solution having a pH of 3.45 as an acidic aqueous solution. This production method is the same as the method disclosed in Non-Patent Document 2.

Comparative Example 2

A specimen was produced under the same conditions as those used in Example 1 except for failing to do heating.

Comparative Example 3

A specimen was produced under the same conditions as those used in Example 1 except for adjusting the holding temperature of the electric furnace to 400° C.

Comparative Example 4

A specimen was produced under the same conditions as those used in Example 1 except for adjusting the holding temperature of the electric furnace to 800° C.

Comparative Example 5

A specimen was produced under the same conditions as those used in Example 5 except for failing to do heating.

Comparative Example 6

A pure titanium metal plate identical to that used in Example 1 was polished and washed in the same manner as in Example 1. Then, the plate was immersed in 10 ml of a mixed solution (pH=1) made up of 8.8 M hydrogen peroxide $H_2O_2$ and 0.1M hydrochloric acid HCl at 80° C. for 30 minutes, and washed with ultrapure water for 30 seconds. Then, this plate was put into a SiC electric furnace and the temperature thereof was increased in air up to 400° C. at a rate of 5° C./min, held at 400° C. for one hour, and then allowed to cool in the furnace, so that a specimen was produced. This production method is the same as one that exhibits the best apatite-forming ability among the methods disclosed in Non-Patent Document 3.

Comparative Example 7

A pure titanium metal plate the same as that used in Example 1 was polished and washed in the same manner as in Example 1. Then, the plate was immersed in a solution prepared by mixing 98% $H_2SO_4$, 36% HCl and water in a volume ratio of 1:1:1 at 60° C. for 1 hour, and washed for 15 minutes in ion exchange water with ultrasonic waves applied. Then, this plate was immersed in 20 ml of a solution (pH≈0) prepared by mixing 65% $HNO_3$ and water in a volume ratio of 1:1, at 60° C. for 600 minutes, and it was washed for 15 minutes in ion exchange water with ultrasonic waves applied, so that a specimen was produced. This production method is the same as one that exhibits the best apatite-forming ability among the methods disclosed in Non-Patent Document 5.

Comparative Example 8

A pure titanium metal plate identical to that used in Example 1 was polished in the same manner as in Example 1, and washed for 2 minutes in 10 ml of a solution prepared by mixing 48% HF, 62% $HNO_3$ and water in a volume ratio of 1:1.5:6. Then, this plate was immersed at 40° C. for 1 hour in 20 ml of a solution (pH≈0) prepared by mixing 97% $H_2SO_4$ and 30% $H_2O_2$ in a volume ratio of 1:1, washed with distilled water, heated to 400° C. at a rate of 5° C./min in a furnace, held for 1 hour and allowed to cool in the furnace, so that a specimen was produced. This production method is the same as that disclosed in Non-Patent Document 6.

Comparative Example 9

A pure titanium metal plate identical to that used in Example 1 was polished and washed in the same manner as in Example 1, and then immersed at 60° C. for 1 hour in 20 ml of an aqueous solution (pH≈0) prepared by mixing 98% $H_2SO_4$, 36% HCl and water in a volume ratio of 1:1:1. Then, the plate was washed for 15 minutes in ion exchange water with ultrasonic waves applied, and then heated under the same conditions as those used in Example 1. This production method is the same as one of the methods disclosed in Non-Patent Document 7.

(Identification of a Phase Constituting a Surface Layer)

The phases constituting the surface layers of the specimens of the examples and the comparative examples were examined by thin film X-ray diffractometry. As a result, anatase-form or rutile-form titanium oxide ($TiO_2$), titanic acid ($H_2Ti_3O_7$), titanium hydride ($TiH_2$), or the like were deposited on the surface of each plate as shown in Table 1. The specimens that exhibited a high apatite-forming ability in a simulated body fluid (Examples 1 to 5) deposited anatase-form or rutile-form titanium oxide. However, some of the specimens that deposited titanium oxide did not exhibit a high apatite-forming ability (Comparative Examples 1, 4, 6, 8 and 9).

(Measurement of Scratch Resistance)

Using a scratch testing machine CSR-2000 manufactured by Rhesca Corporation, vibration 100 μm in amplitude was added to a stylus with a spring constant of 200 g/mm on a specimen, and the stylus was moved at a rate of 10 mm/sec under a load increasing at a rate of 100 mN/min. A critical scratch load at this time was measured as a scratch resistance. As a result, as shown in Table 1, specimens heated at temperatures of 600° C. to 700° C. (Examples 1 to 5, Comparative Examples 1 and 9) exhibited high values of 40 mN or more, whereas non-heated specimens (Comparative Examples 2, 5, and 7), specimens heated at 400° C. or lower (Comparative Examples 3, 6, and 8) and a specimen heated at 800° C. or higher (Comparative Example 4) exhibited values of only 33 mN or less.

(Measurement of Zeta Potential)

The specimens of the examples and the comparative examples were immersed in a 10 mM aqueous sodium chloride NaCl solution, and a zeta potential was measured with a laser electrophoresis apparatus (Otsuka Electronics, model ELS-ZI) by using polystyrene latex particles as monitor particles. The measurement results are shown in Table 1. Of the measured data given in the table, the data indicated on the left of virgules were obtained after discharging the specimens by grounding, and the data indicated on the right of the virgules were obtained without doing such a discharging treatment. As shown in the table, all the specimens of the examples exhibited positive zeta potentials as high as 5.0 mV or more, whereas all the specimens of the comparative examples exhibited zeta potentials of only 4.0 mV or less. In Table 1, zeta potentials are indicated also for the non-heated specimens. However, since non-heated specimens exhibit high electrical conductivities, they hardly store charges. Therefore, the zeta potentials having small absolute values measured for the non-heated specimens mean that they are approximately zero regardless of whether they are positive or negative.

(Measurement of Adsorption of Ions)

Figure 4:
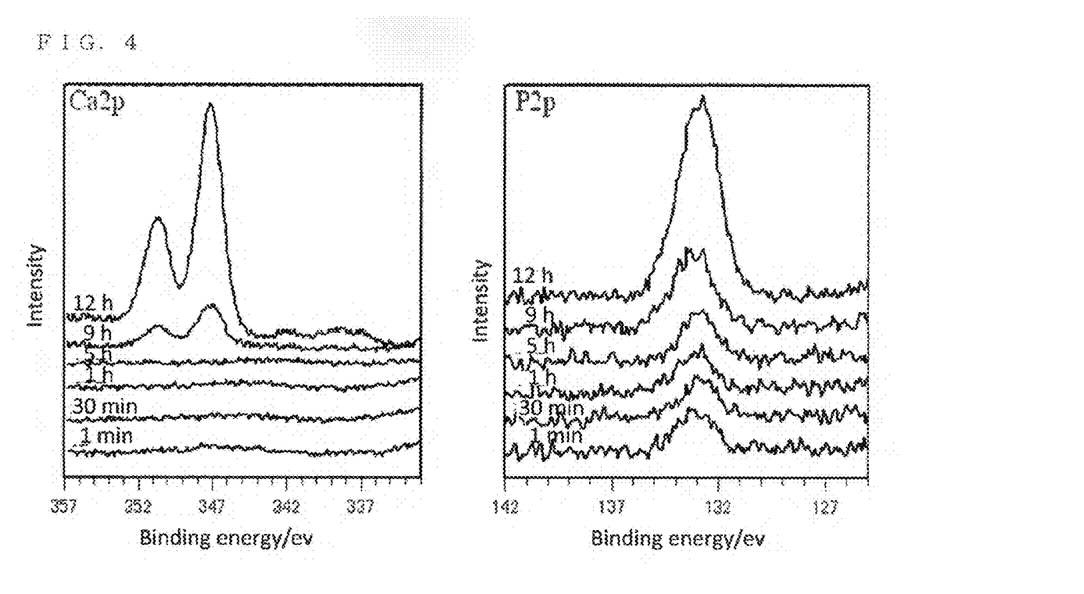
FIG. 4 shows X-ray photoelectron spectra of a surface of the specimen of Example 1 immersed in a simulated body fluid (SBF) for various lengths of times.

The specimen of Example 1 was immersed in a simulated body fluid of ISO 23317 for various lengths of times and followed by subjecting the surface of the specimen to X-ray photoelectron spectroscopic analysis. As a result, a phenomenon that phosphate ions were adsorbed first onto the specimen and then calcium ions were adsorbed as shown in FIG. 4 was observed. According to the same analysis conducted for the other specimens, phosphate ions were adsorbed first and then calcium ions were adsorbed for the specimens of all the examples as shown in Table 1. This is because all of these specimens are positively charged on their surfaces and have high zeta potentials and, therefore, negatively charged phosphate ions are adsorbed first and then positively charged calcium ions are adsorbed as the surfaces of the specimens are charged negatively by the phosphate ions. On the other hand, for all the specimens of the comparative examples other than Comparative Examples 1, 4, 6, and 9, phosphate ions and calcium ions are adsorbed almost at the same time or calcium ions are adsorbed earlier than phosphate ions.

(Evaluation of Apatite-Forming Ability)

Figure 5:
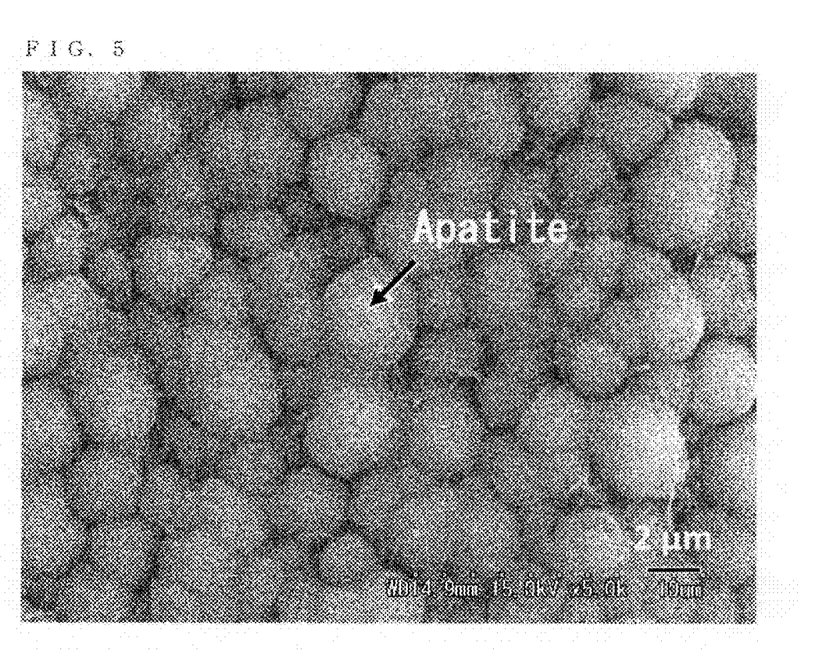
FIG. 5 is a scanning electron-microphotograph of a surface of the specimen of Example 1 immersed in the SBF for 1 day.
Figure 6:
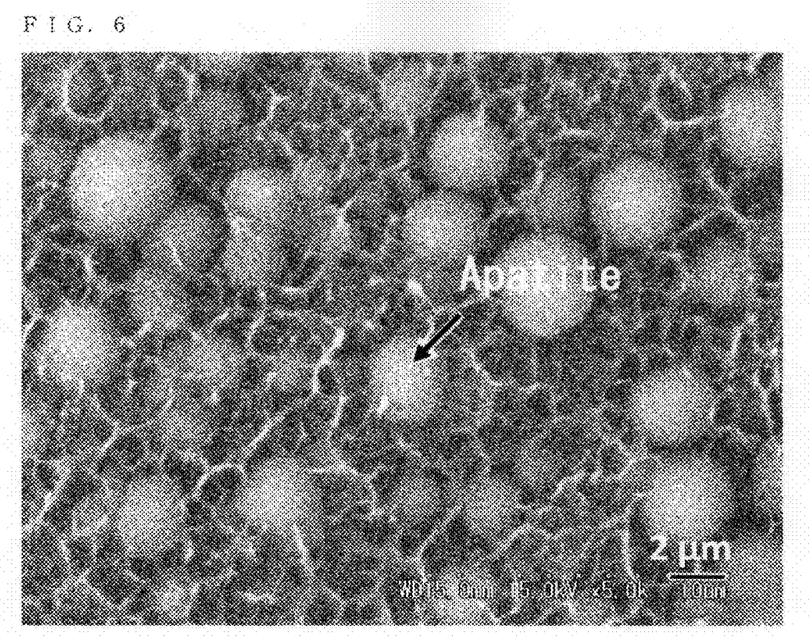
FIG. 6 is a scanning electron microphotograph of a surface of the specimen of Comparative Example 1 immersed in the SBF for 1 day.

When the specimen of Example 1 was immersed in a simulated body fluid (SBF) of ISO 23317 kept at 36.5° C., the surface thereof was covered thoroughly with apatite within one day as shown in FIG. 5. When this apatite-forming ability is represented by +++, the specimens of all the examples had apatite-forming abilities of +++ as shown in Table 1. On the other hand, when the specimen of Comparative Example 1 was immersed in SBF in a similar manner, the surface thereof was covered with apatite only sparsely within one day as shown in FIG. 6. When an apatite-forming ability of such a degree is represented by ++, the specimens of all the comparative examples had apatite-forming abilities of only 0, +, or ++ as shown in Table 1. It is noted that 0 means that apatite was not formed at all and + represents an apatite-forming ability as weak as apatite can be only barely found.

TABLE 1

| Specimen *1 | Process | Phase | Scratch R (mN) | Zeta potential (mV) | Absorpption of ions | Apatite-forming ability |
|---|---|---|---|---|---|---|
| E 1 | Alkali - 50 mM HCl (pH = 1.47) - 600 C. | Anatase + Rutile | 50 | +8.0/+10.7 | P→Ca | +++ |
| E 2 | Alkali - 50 mM HCl (pH = 1.47) - 700 C. | Rutile + Anatase | 50 | +13.0/+16.0 | P→Ca | +++ |
| E 3 | Alkali - 50 mM $HNO_3$ (pH = 1.46) - 600 C. | Rutile + Anatase | 50 | +10.0/+14.7 | P→Ca | +++ |
| E 4 | Alkali - 10 mM $H_2SO_4$ (pH = 1.98) - 600 C. | Anatase + Rutile | 50 | +5.0/+6.6 | P→Ca | +++ |
| E 5 | $H_2SO_4$/HCl (pH ≈ 0) - 600 C. | Rutile | 40 | +5.0/+7.0 | P→Ca | +++ |
| C 1 | Alkali - 0.5 mM HCl (pH = 3.45) - 600 C. | Anatase + Rutile | 50 | /+3.2 | P→Ca | ++ |
| C 2 | Alkali - 50 mM HCl (pH = 1.47) - non-heating | titanic acid($H_2Ti_3O_7$) | 5 | /−1.0 | Ca→P | + |
| C 3 | Alkali - 50 mM HCl (pH = 1.47) - 400 C. | titanic acid($H_2Ti_3O_7$) + Anatase | 10 | /−1.0 | Ca=P | ++ |
| C 4 | Alkali - 50 mM HCl (pH = 1.47) - 800 C. | Rutile | 33 | +4.0/+5.0 | P→Ca | ++ |
| C 5 | $H_2SO_4$/HCl (pH ≈ 0) - non-heating | $TiH_2$ | 4 | /+1.5 | Ca=P | 0 |
| C 6 | $H_2O_2$/HCl(pH = 1) - 400 C. | Anatase | 13 | +4.0/+5.0 | P→Ca | ++ |
| C 7 | $H_2SO_4$/HCl—$HNO_3$ (pH ≈ 0) - non-heating | Ti | 5 | /+2.1 | Ca=P | + |
| C 8 | $H_2SO_4$/$H_2O_2$(pH ≈ 0) - 400 C. | Ti | 8 | /−1.4 | Ca=P | + |
| C 9 | $H_2SO_4$/HCl(pH ≈ 0) - washing - 600 C. | Rutile | 40 | +4.0/+5.0 | P→Ca | + |

*1: E and C denote Example and Comparative Example, respectively.

(Reconfirmation of Charged Surface)

Figure 7:
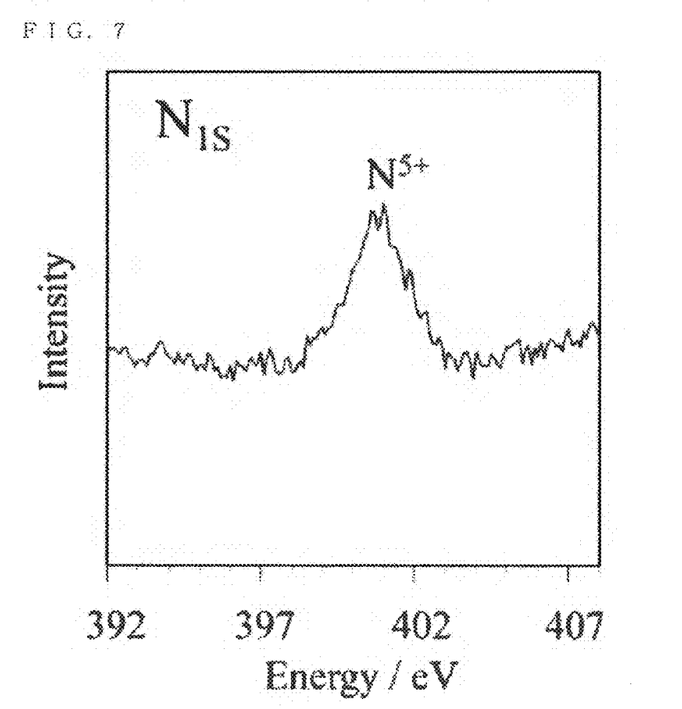
FIG. 7 is a spectrum that shows the result obtained by analyzing a surface of the specimen of Example 3 by X-ray photoelectron spectroscopy (XPS).
Figure 8:
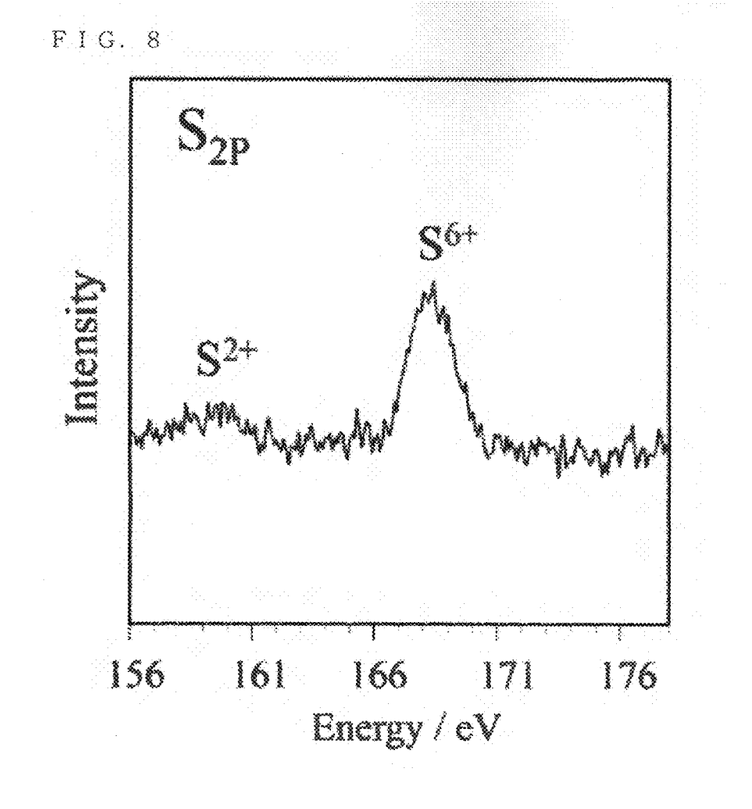
FIG. 8 is a spectrum that shows the result obtained by analyzing a surface of the specimen of Example 4 by X-ray photoelectron spectroscopy (XPS).

When the surfaces of the specimens of Examples 3 and 4 were analyzed by X-ray photoelectron spectroscopy (XPS), nitrogen atoms were detected on the specimen surface of Example 3 and sulfur atoms were detected on the specimen surface of Example 4 as the analysis results are shown in FIGS. 7 and 8, respectively, by XPS spectra. This means that atoms of sulfur or nitrogen that constitute anions, such as sulfate ions, nitrate ions, and chloride ions, that form a pair with a positive charge are adsorbed onto the surface of titanium oxide that constitutes a surface layer, and proves that a positive zeta potential is observed and also that acid groups remain on the surface of titanium oxide.

The invention claimed is:

1. A bone repair material comprising:
 a substrate made of titanium or titanium alloys, the substrate having on the surface thereof irregularities of from 1 nm to 10 μm in average in both width and depth; and
 a surface layer along the surface of the substrate, the surface layer consisting essentially of titanium oxide and having a zeta potential of +4.5 mV or more under an aqueous solution environment of pH 6 to 8.

2. The bone repair material according to claim 1, wherein the surface layer has a critical scratch resistance of 35 mN or more when vibration 100 μm in amplitude is added to a stylus with a spring constant of 200 g/mm on the surface layer and the stylus is moved at a rate of 10 mm/sec under a load increasing at a rate of 100 mN/min.

3. The bone repair material according to claim 1, wherein the surface layer contains an acid group constituting an acid.

4. A method for producing the bone repair material of claim 1, the method comprising the steps of:
 preparing a substrate made of titanium or titanium alloys;
 forming irregularities of from 1 nm to 10 μm in average in both width and depth on the surface of the substrate;
 immersing the substrate in an acidic aqueous solution having a pH of 3 or less;
 washing the substrate with water after the immersion; and thereafter
 heating the substrate at a temperature of 450 to 750° C.

5. The method according to claim 4, wherein the formation of the irregularities is conducted by an alkali treatment.

6. The method according to claim 4, wherein the acidic aqueous solution is a solution selected from the group consisting of aqueous solutions of hydrochloric acid, sulfuric acid, nitric acid, fluoric acid, and mixed acid thereof.

7. The method according to claim 4, wherein the formation of the irregularities is conducted by performing a treatment with an acidic aqueous solution that is the same as or different from the acidic aqueous solution.

8. The method according to any one of claims 4 to 7, wherein the washing time is from 10 seconds to 1 minute.

* * * * *